United States Patent [19]
Eicken et al.

[11] Patent Number: 6,130,224
[45] Date of Patent: Oct. 10, 2000

[54] FUNGICIDAL AGENTS AND METHOD

[75] Inventors: Karl Eicken, Wachenheim; Harald Köhle, Bobenheim; Günter Retzlaff, Römerberg; Eberhard Ammermann, Heppenheim; Gisela Lorenz, Hambach; Siegfried Strathmann, Limburgerhof, all of Germany

[73] Assignee: BASF Aktiengesellschaft, Ludwigshafen, Germany

[21] Appl. No.: 09/029,629

[22] PCT Filed: Sep. 5, 1996

[86] PCT No.: PCT/EP96/03861

§ 371 Date: Mar. 4, 1998

§ 102(e) Date: Mar. 4, 1998

[87] PCT Pub. No.: WO97/08952

PCT Pub. Date: Mar. 13, 1997

[30] Foreign Application Priority Data

Sep. 5, 1995 [DE] Germany ............................ 195 32 752

[51] Int. Cl.[7] ............................ A01N 43/40; A01N 43/54
[52] U.S. Cl. ............................................ 514/259; 514/355
[58] Field of Search ...................................... 514/259, 355

[56] References Cited

U.S. PATENT DOCUMENTS

| 5,330,995 | 7/1994 | Eicken et al. | 514/355 |
| 5,411,963 | 5/1995 | Dreikorn et al. | 514/259 |
| 5,438,070 | 8/1995 | Eicken et al. | 514/403 |

FOREIGN PATENT DOCUMENTS

| 545099 | 6/1993 | European Pat. Off. . |
| 589301 | 3/1994 | European Pat. Off. . |
| 93/11117 | 6/1993 | WIPO . |

OTHER PUBLICATIONS

*The Pesticide Manual*, Tenth Edition, Entry 290, pp. 426–427, 1994. Tomlin.

*Primary Examiner*—Allen J. Robinson
*Attorney, Agent, or Firm*—Keil & Weinkauf

[57] ABSTRACT

The present invention relates to composiitons for controlling harmful fungi which comprise, as active ingredients, fenazaquin and at least one amide compound of the formula I $$A\text{—}CO\text{—}NR^1R^2 \qquad I$$

where A, $R^1$ and $R^2$ have the meanings given in the description. The compositions according to the invention are particularly useful for controlling botrytis.

16 Claims, No Drawings

FUNGICIDAL AGENTS AND METHOD

This application is a 371 of PCT/EP96/03861, filed Sep. 5, 1996.

The present invention relates to compositions for controlling harmful fungi and to methods of controlling harmful fungi using such compositions.

EP-A-545 099 describes analide compounds of the formula

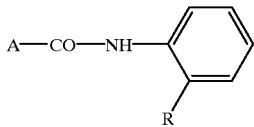

where A is phenyl which is substituted in the 2-position by methyl, trifluoromethyl, chlorine, bromine or iodine, or is a certain aromatic or non-aromatic heterocyclic radical which can be unsubstituted or substituted by methyl, chlorine or trifluoromethyl, and R is a certain aliphatic or cycloaliphatic radical which can be unsubstituted or substituted by halogen, or is phenyl which is unsubstituted or substituted by $C_1$–$C_4$-alkyl, $C_1$–$C_4$-alkoxy, $C_1$–$C_4$-alkylthio or halogen. These compounds are useful for controlling botrytis.

EP-A-589 301 describes analide compounds of the same formula where A is a cyclic radical of the formulae:

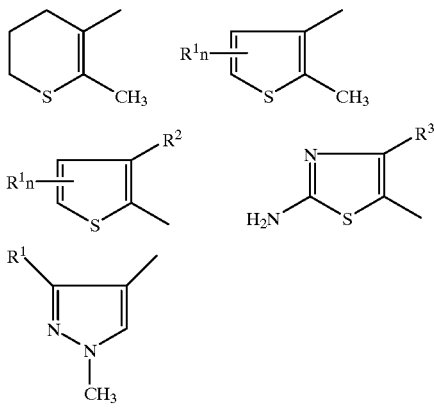

where $R^1$ is hydrogen or $C_1$–$C_4$-alkyl; $R^2$ is halogen or $C_1$–$C_4$-alkyl; $R^3$ is $C_1$–$C_4$-alkyl or $C_1$–$C_4$-haloalkyl; n is 1 or 2; and R has essentially the meanings given above. These compounds are also useful for the treatment of botrytis.

WO 93/11117 describes compounds of the formula

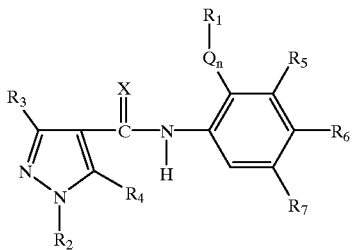

where
Q is $C_1$–$C_3$-alkyl, $C_2$–$C_3$-alkenyl, $C_2$–$C_3$-alkynyl, —(CH$_2$)$_m$CH= or —(CH$_2$)$_m$—X—CH$_2$)m—;
n is 0 or 1;
each m independently of the others is 0, 1, 2 or 3;
each x independently is O or S;
$R^1$ is a certain alicyclic radical;
$R^2$ is hydrogen, fluorinated methyl, methyl, ethyl, $C_2$–$C_6$-alkenyl, $C_3$–$C_6$-chloroalkyl, phenyl, alkylthioalkyl, alkoxyalkyl, haloalkylthioalkyl, haloalkoxyalkyl or hydroxyalkyl;
$R^3$ is halomethyl, halomethoxy, methyl, ethyl, halogen, cyano, methylthio, nitro, aminocarbonyl or aminocarbonylmethyl;
$R^4$ is hydrogen, halogen or methyl;
$R^5$, $R^6$ and $R^7$ in each case independently of the other are selected from amongst hydrogen, halogen, cyano, $C_1$–$C_6$-alkyl, $C_2$–$C_6$-alkenyl, $C_2$–$C_6$-alkynyl, $C_1$–$C_4$-alkoxy, $C_1$–$C_4$-alkylthio, $C_3$–$C_4$-cycloalkyl and halomethoxy. These compounds are fungicidally active.

It is an object of the present invention to provide a better possibility of controlling harmful fungi, in particular botrytis.

Surprisingly, we have found that this object is achieved by a composition which comprises, as active ingredients, fenazaquin, which is known as an acaricide (The Pesticide Manual, 10th Edition, 1994; CAS Reg. No. 120928-09-8), and amide compounds of the formula I described below.

The present invention therefore relates to compositions for controlling harmful fungi which comprise, in a solid or liquid carrier, fenazaquin, of the formula:

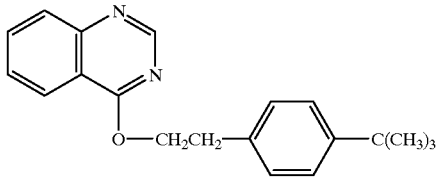

and at least one amide compound of the formula I below:

where
A is an aryl group or an aromatic or non-aromatic, 5- or 6-membered heterocycle having 1 to 3 hetero atoms selected from amongst O, N and S; it being possible for the aryl group or the heterocycle to be unsubstituted or to have 1, 2 or 3 substituents which, independently of one another, are selected from amongst alkyl, halogen, CHF$_2$, CF$_3$, alkoxy, haloalkoxy, alkylthio, alkylsulfinyl and alkylsulfonyl;
$R^1$ is a hydrogen atom;
$R^2$ is a phenyl or cycloalkyl group which is unsubstituted or has 1, 2 or 3 substituents which are selected from amongst alkyl, alkenyl, alkynyl, alkoxy, alkenyloxy, alkyloxy, cycloalkyl, cycloalkenyl, cycloalkyloxy, cycloalkenyloxy, phenyl and halogen, it being possible for the aliphatic and cycloaliphatic radicals to be partially or fully halogenated and/or for the cycloaliphatic radicals to be substituted by 1 to 3 alkyl groups, and it being possible for the phenyl group to have 1 to 5 halogen atoms and/or 1 to 3 substituents which, independently of one another, are selected from amongst alkyl, haloalkyl, alkoxy, haloalkoxy, alkylthio and haloalkylthio, and it being possible for the amidic phenyl group to be fused to a saturated 5-membered ring which is unsubstituted or substituted by one or more alkyl groups and/or can have a hetero atom selected from amongst O and S.

The compositions according to the invention act synergistically and are therefore particularly suitable for controlling harmful fungi, in particular botrytis.

In the scope of the present invention, halogen is fluorine, chlorine, bromine and iodine, in particular fluorine, chlorine and bromine.

The term "alkyl" embraces straight-chain and branched alkyl groups. They are preferably straight-chain or branched $C_1$–$C_{12}$-alkyl groups, in particular $C_1$–$C_6$-alkyl groups. Examples of alkyl groups are alkyl such as, in particular, methyl, ethyl, propyl, 1-methylethyl, butyl, 1-methylpropyl, 2-methylpropyl 1,1-dimethylethyl, n-pentyl, 1-methylbutyl, 2-methylbutyl, 3-methylbutyl, 1,2-dimethylpropyl, 1,1-dimethylpropyl, 2,2-dimethylpropyl, 1-ethylpropyl, n-hexyl, 1-methylpentyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 1-methylhexyl, 1-ethylpentyl, 2-ethylpentyl, 1-propylbutyl, octyl, decyl, dodecyl.

Haloalkyl is an alkyl group as defined above which is partially or fully halogenated by one or more halogen atoms, in particular fluorine and chlorine. There are preferably 1 to 3 halogen atoms, the difluoromethyl group or trifluoromethyl group being especially preferred.

What has been said above about the alkyl group and haloalkyl group applied analogously to the alkyl and haloalkyl group in alkoxy, haloalkoxy, alkylthio, haloalkylthio, alkylsulfinyl and alkylsulfonyl.

the alkenyl group embraces straight-chain and branched alkenyl groups. They are preferably straight-chain or branched $C_3$–$C_{12}$-alkenyl groups, in particular $C_3$–$C_6$-alkenyl groups. Examples of alkenyl groups are 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl and 1-ethyl-2-methyl-2-propenyl, in particular 2-propenyl, 2-butenyl, 3-methyl-2-butenyl and 3-methyl-2-pentenyl.

The alkenyl group can be partially or fully halogenated by one or more halogen atoms, in particular fluorine and chlorine. It has preferably 1 to 3 halogen atoms.

The alkynyl group embraces straight-chain and branched alkynyl groups. They are preferably straight-chain and branched $C_3$–$C_{12}$-alkynyl groups, in particular $C_3$–$C_6$-alkynyl groups. Examples of alkynyl groups are 2-propynyl, 2-butynyl, 3-butynyl, 1-methyl-2-propynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-alkynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,2-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl and 1-ethyl-1-methyl-2-propynyl.

What has been said above about the alkenyl group and its halogen substituents and about the alkynyl group applied analogously to alkenyloxy and alkynyloxy.

The cycloalkyl group is preferably a $C_3$–$C_6$-cycloalkyl group, such as cyclopropyl, cyclobutyl, cyclopentyl or cyclohexyl. If the cycloalkyl group is substituted, it preferably has 1 to 3 $C_1$–$C_4$-alkyl radicals as substituents.

Cycloalkenyl is preferably a $C_4$–$C_6$-cycloalkenyl group, such as cyclobutenyl, cyclopentenyl or cyclohexenyl. If the cycloalkenyl group is substituted, it has preferably 1 to 3 $C_1$–$C_4$-alkyl radicals as substituents.

A cycloalkoxy group is preferably a $C_5$–$C_6$-cycloalkoxy group, such as cyclopentyloxy or cyclohexyloxy. If the cycloalkoxy group is substituted, it preferably has 1 to 3 $C_1$–$C_4$-alkyl radicals as substituents.

The cycloalkenyloxy group is preferably a $C_5$–$C_6$-cycloalkenyloxy group, such as cyclopentyloxy or cyclohexyloxy. If the cycloalkenyloxy group is substituted, it preferably has 1 to 3 $C_1$–$C_4$-alkyl radicals as substituents.

Aryl is preferably phenyl.

If A is a phenyl group, this group can have one, two or three of the abovementioned substituents in any position. These substituents are preferably selected independently of one another from amongst alkyl, difluoromethyl, trifluoromethyl and halogen, in particular chlorine, bromine and iodine. The phenyl group especially preferably has a substituent in the 2-position.

If A is a 5-membered heterocycle, the heterocycle is, in particular, a furyl, thiazolyl, pyrazolyl, imidazolyl, oxazolyl, thienyl, trizaolyl or thiadiazolyl radical or the corresponding dihydro or tetrahydro derivatives thereof. A thiazolyl or pyrazolyl radical is preferred.

If A is a 6-membered heterocycle, this heterocycle is, in particular, a pyridyl radical or a radical of the formula:

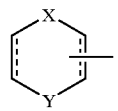

where one of the radicals X and Y is O, S or $NR^9$, $R^9$ being H or alkyl, and the other of the radicals X and Y is $CH_2$, S, SO, $SO_2$ or $NR^9$. The broken line indicates that a double bond may be present.

The 6-membered aromatic heterocycle is especially preferably a pyridyl radical, in particular a 3-pyridyl radical, or a radical of the formula (A3)

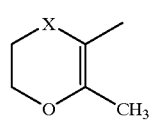

where X is $CH_2$, S, SO or $SO_2$.

The abovementioned heterocyclic radicals can be unsubstituted or have 1, 2 or 3 of the abovementioned substituents, these substituents preferably being selected, independently of one another, from amongst alkyl, halogen, difluoromethyl or trifluoromethyl.

A is especially preferably a radical of the formulae:

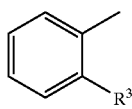
(A1)

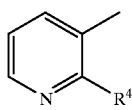
(A2)

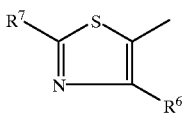
(A5)

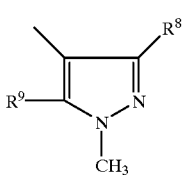
(A7)

where $R^3$, $R^4$, $R^6$, $R^7$, $R^8$ and $R^9$ independently of one another are hydrogen, alkyl, in particular methyl, halogen, in particular chlorine, $CHF_2$ or $CF_3$.

The radical $R^1$ in formula I is preferably a hydrogen atom.

The radical $R^2$ in the formula I is preferably a phenyl radical. $R^2$ preferably has at least one substituent, particularly preferably in the 2-position, The substituent is (or the substituents are) preferably selected from amongst alkyl, cycloalkyl, cycloalkenyl, halogen or phenyl.

The substituents of radical $R^2$, can, in turn, also be substituted. The aliphatic or cycloaliphatic substituents can be partially or fully halogenated, in particular fluorinated or chlorinated. They preferably have 1, 2 or 3 fluorine or chlorine atoms. If the substituent of the radical $R^2$ is a phenyl group, this phenyl group can be substituted by preferably 1 to 3 halogen atoms, in particular chlorine atoms, and/or by a radical which is preferably selected from amongst alkyl and alkoxy. The phenyl group is particularly preferably substituted by a halogen atom in the p-position, ie. the especially preferred substituent of the radical $R^2$ is a p-halogen-substituted phenyl radical. The radical $R^2$ can also be fused to a saturated 5-membered ring, it being possible for this ring, in turn, to have 1 to 3 alkyl substituents.

In this case, $R^2$ is, for example, indanyl, thiaindanyl and oxaindanyl. Preferred are indanyl and 2-oxaindanyl, which are bonded to the nitrogen atom, in particular, via the 4-position.

In a preferred embodiment, the composition according to the invention comprises, as the amide compound, a compound of the formula I where A has the following meanings: phenyl, pyridyl, dihydropyranyl, dihydrooxathiinyl, dihydrooxathiinyl oxide, dihydrooxathiinyl dioxide, furyl, thiazolyl, pyrazolyl or oxazolyl, it being possible for these groups to have 1, 2 or 3 substituents which, independently of one another, are selected from amongst alkyl, halogen, difluoromethyl and trifluoromethyl.

In a further preferred embodiment, A is:
pyridin-3-yl which is unsubstituted or substituted in the 2-position by halogen, methyl, difluoromethyl, trifluoromethyl, methoxy, methylthio, methylsulfinyl or methylsulfonyl;

phenyl which is unsubstituted or substituted in the 2-position by methyl, trifluoromethyl, chlorine, bromine or iodine;

2-methyl-5,6-dihydropyran-3-yl;

2-methyl-5,6-dihydro-1,4-oxathiin-3-yl or the 4-oxide or 4,4-dioxide thereof;

2-methyl-furan-3-yl which is unsubstituted or substituted in the 4- and/or 5-position by methyl;

thiazol-5-yl which is unsubstituted or substituted in the 2- and/or 4-position by methyl, chlorine, difluoromethyl or trifluoromethyl;

thiazol-4-yl which is unsubstituted or substituted in the 2- and/or 5-position by methyl, chlorine, difluoromethyl or trifluoromethyl;

1-methylpyrazol-4-yl which is unsubstituted or substituted in the 3- and/or 5-position by methyl, chlorine, difluoromethyl or trifluoromethyl; or oxazol-5-yl which is unsubstituted or substituted in the 2- and/or 4-position by methyl or chlorine.

In a further preferred embodiment, the compositions according to the invention comprise, as the amide compound, a compound of the formula I where $R^2$ is a phenyl group which is unsubstituted or substituted by 1, 2 or 3 of the abovementioned substituents.

In a further preferred embodiment, the compositions according to the invention comprise, as the amide compound, a compound of the formula I where $R^2$ is a phenyl group which has one of the following substituents in the 2-position:

$C_3$–$C_6$-alkyl, $C_5$–$C_6$-cycloalkenyl, $C_5$–$C_6$-cycloalkyloxy, cycloalkenyloxy, it being possible for these groups to be substituted by 1, 2 or 3 $C_1$–$C_4$-alkyl groups, phenyl which is substituted by 1 to 5 halogen atoms and/or 1 to 3 groups which are selected, independently of one another, from amongst $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio and $C_1$–$C_4$-haloalkylthio, indanyl or oxaindanyl, each of which is unsubstituted or substituted by 1, 2 or 3 $C_1$–$C_4$-alkyl groups.

In a further preferred embodiment, the compositions according to the invention comprise, as the amide compound, a compound of the formula Ia

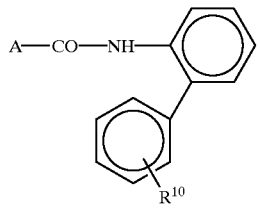
(Ia)

where

A is

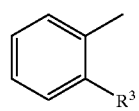
(A1)

-continued

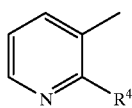
(A2)

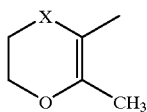
(A3)

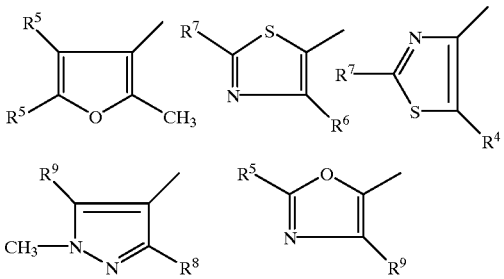

X is methylene, sulfur, sulfinyl or sulfonyl ($SO_2$),
$R^3$ is methyl, difluoromethyl, trifluoromethyl, chlorine, bromine or iodine,
$R^4$ is trifluoromethyl or chlorine,
$R^5$ is hydrogen or methyl,
$R^6$ is methyl, difluoromethyl, trifluoromethyl or chlorine,
$R^7$ is hydrogen, methyl or chlorine,
$R^8$ is methyl, difluoromethyl or trifluoromethyl,
$R^9$ is hydrogen, methyl, difluoromethyl, trifluoromethyl or chlorine,
$R^{10}$ is $C_1$–$C_4$-alkyl, $C_1$–$C_4$-alkoxy, $C_1$–$C_4$-alkylthio or halogen.

In an especially preferred embodiment, the compositions comprise, as the amide compound, a compound of the formula Ib

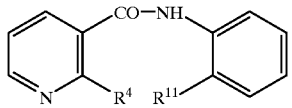
(Ib)

where
$R^4$ is halogen and
$R^{11}$ is phenyl which is substituted by halogen.

Useful amide compounds are mentioned in EP-A-545 099 and 589 301, which are herewith referred to in their entirety.

The preparation of the amide compounds of the formula I is disclosed, for example, in EP-A-545 099 or 589 301 or can be carried out by similar processes.

Even a small amount of amide compound of the formula I suffices to act synergistically. Preferably, fenazaquin and the amide compound are employed in a weight ratio in a range of 20:1 to 1:20, in particular 10:1 to 1:10.

The invention also relates to a method of controlling harmful fungi, which comprises treating the fungi, their environment, or the materials, plants, seeds, soils, areas of spaces to be protected against fungal infection, with a composition as claimed in any of claims 1 to 9, it being possible to apply the active ingredients fenazaquin and amide compound simultaneously, ie. concomitantly or separately, or in succession.

For example, the compositions according to the invention can be applied in the form of directly sprayable solutions, powders, suspensions, also highly concentrated aqueous, oily or other suspensions or dispersion, emulsions, oil dispersions, pastes, dusts, materials for spreading, or granules, by means of spraying, atomizing, dusting, spreading or pouring. The use forms depend on the intended purposes; in any case, they should guarantee the finest possible distribution of the active ingredients according to the invention.

Normally, the plants are sprayed or dusted with the active ingredients, or the seeds of the plants are treated with the active ingredients.

The formulations are prepared in a known manner, eg. by extending the active ingredient with solvents and/or carries, if desired using emulsifiers and dispersants, it also being possible to use other organic solvents as auxiliary solvents if water is used as the diluent. Auxiliaries are essentially: solvents such as aromatics (eg. xylene), chlorinated aromatics (eg. chlorobenzenes), paraffins (eg. mineral oil fractions), alcohols (eg. methanol, butanol), ketones (eg. cyclohexanone), amines (eg. ethanolamine, dimethylformamide) and water; carriers such as ground natural minerals (eg. kaolins, clays, talc, chalk) and ground synthetic minerals (eg. highly-disperse silica, silicates); emulsifiers such as non-ionic and anionic emulsifiers (eg. polyoxyethylene fatty alcohol ethers, alkylsulfonates and arylsulfonates) and dispersants, such as lignosulfite water liquors and methylcellulose.

Suitable surfactants are the alkali, alkaline earth and ammonium salts of aromatic sulfonic acids, eg. ligno-, phenol-, naphthalene- and dibutylnaphthalene-sulfonic acid, and of fatty acids, alkyl- and alkylaryl-sulfonates, alkyl, lauryl ether and fatty alcohol sulfates, and also salts of sulfated hexa-, hepta- and octadecanols, and fatty alcohol glycol ethers, condensates of sulfonated naphthalene and its derivatives with formaldehyde, condensates of naphthalene, or of the naphthalenesulfonic acids, with phenol and formaldehyde, polyoxyethylene octylphenol ether, ethoxylated isoctyl-, octyl- or nonylphenyl, alkylphenyl polyglycol ethers, tributylphenyl polyglycol ether, alkylaryl polyether alcohols, isotridecyl alcohol, fatty alcohol/ethylene oxide condensates, ethoxylated castor oil, polyoxyethylene alkyl ethers or polyosypropylene alkyl ethers, lauryl alcohol polyglycol ether acetate, sorbitol esters, lignin-sulfite water liquors or methylcellulose.

Powders, materials for spreading and dusts, can be prepared by mixing or concomitantly grinding the active ingredients together with a solid carrier.

Granules, eg. coated granules, impregnated granules and homogeneous granules, can be prepared by binding the active ingredients to solid carriers. Solid carriers are mineral earths such as silica gel, silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate, ammonium nitrate, ureas, and products of vegetable origin, such as cereal meal, tree bark meal, wood meal and nutshell meal, cellulose powders, or other solid carriers.

Examples of such preparations which comprise the active ingredients fenazaquin and amide compound in a weight ratio of 8:1 are:

I. a solution of 90 parts by weight of the active ingredients and 10 parts by weight of N-methyl-pyrrolidone, this solution being suitable for use in the form of microdrops;

II. a mixture of 20 parts by weight of the active ingredients, 80 parts by weight of xylene, 10 parts by weight of the adduct of 8 to 10 mol of ethylene oxide to 1 mol of oleic acid N-monoethanolamide, 5 parts by weight of calcium dodecylbenzenesulfonate, 5 parts by weight of the adduct of 40 mol of ethylene oxide to 1 mol of castor oil; a dispersion is obtained by finely distributing the solution in water;

III. an aqueous dispersion of 20 parts by weight of the active ingredients, 40 parts by weight of cyclohexanone, 30 parts by weight of isobutanol, 20 parts by weight of the adduct of 40 ml of ethylene oxide to 1 mol of castor oil;

IV. an aqueous dispersion of 20 parts by weight of the active ingredients, 25 parts by weight of cyclohexanol, 65 parts by weight of a mineral oil fraction of boiling point 210 to 280° C. and 10 parts by weight of the adduct of 40 mol of ethylene oxide to 1 mol of castor oil;

V. a mixture, ground in a hammer mill, of 80 parts by weight of the active ingredients, 3 parts by weight of sodium diisobutylnaphthalene-1-sulfonate, 10 parts by weight of the sodium salt of a lignosulfonic acid from a sulfite waste liquor and 7 parts by weight of pulverulent silica gel; a spray mixture is obtained by finely distributing the mixture in water;

VI. an intimate mixture of 3 parts by weight of the active ingredients and 97 parts by weight of finely divided kaolin; this dust comprises 3% by weight of active ingredient;

VII. an intimate mixture of 30 parts by weight of the active ingredients, 92 parts by weight of pulverulent silica gel and 8 parts by weight of paraffin oil which has been sprayed onto the surface of this silica gel; this formulation imparts good adherence properties to the active ingredient;

VIII. a stable aqueous dispersion of 40 parts by weight of the active ingredients, 10 parts by weight of the sodium salt of a phenolsulfonic acid/urea/formaldehyde condensate, 2 parts by weight of silica gel and 48 parts by weight of water; this dispersion can be diluted further;

IX. a stable oily dispersion of 20 parts by weight of the active ingredients, 2 parts by weight of calcium dodecylbenzenesulfonate, 8 parts by weight of fatty alcohol polyglycol ether, 20 parts by weight of the sodium salt of a phenolsulfonic acid/urea/ formaldehyde condensate and 88 parts by weight of a paraffinic mineral oil.

The compositions according to the invention have an outstanding activity against a broad spectrum of phytopathogenic fungi, in particular against botrytis. In some cases, they act systemically (ie. they can be taken up by the treated plant without loss of efficacy and, if appropriate, translocated within the plant) and can be employed as foliar- and soil-acting fungicides.

They are especially important for controlling a large number of fungi in a variety of crop plants such as wheat, rye, barley, oats, rice, maize, grass, cotton, soya, coffee, sugar cane, grapevines, fruit species, ornamentals and vegetable species such as cucumbers, beans and cucurbits, and the seeds of these plants.

The compositions are applied by treating the fungi, or the seeds, plants, materials or the soil to be protected against fungal infection, with a fungicidally active amount of the active ingredients.

Application is effected before or after infection of the materials, plants or seeds by the fungi.

Specifically, the compositions are suitable for controlling the following plant diseases:

*Erysiphe graminis* (powdery mildew) in cereals,
*Erysiphe cichoracearum* and *Sphaerotheca fuliginea* in cucurbits,
*Podosphaera leucotricha* in apples,
*Uncinula necator* in grapevines,
*Venturia inaequalis* (scab) in apples,
Helminthosporium species in cereals,
*Septoria nodorum* in wheat,
*Botrytis cinerea* (gray mold) in strawberries and grapevines,
*Cercospora arachidicola* in groundnuts,
*Pseudocercosporella herpotrichoides* in wheat and barley,
*Pyricularia oryzae* in rice,
Fusarium and Verticillium species in a variety of plants,
Alternaria species in vegetables and fruit,
Monilinia species in fruit, and
Schlerotinia species in oil seed rape and vegetables.

The use against botrytis is preferred.

The compositions can also be employed in the protection of materials (protection of wood), eg. against *Paecilomyces variotii*.

In general, the fungicidal compositions comprise from 0.1 to 95, preferably from 0.5 to 90, % by weight of active ingredient.

Depending on the nature of the desired effect, the rates of application are from 0.02 to 3 kg of active ingredient per ha.

In the treatment of seed, amounts of active ingredient of from 0.001 to 50 g, preferably 0.01 to 10 g, are generally required per kilogram of seed.

In the use form as fungicides, the compositions according to the invention can also comprise other active ingredients, eg. herbicides, insecticides, growth regulators, fungicides or else fertilizers. A mixture with fungicides in many cases results in a widened fungicidal spectrum of action.

The following list of fungicides together with which the compounds according to the invention can be used is intended to illustrate the possible combinations, but not to impose any limitation:

sulfur,
dithiocarbamates and their derivatives, such as
iron(III) dimethyldithiocarbamate,
zinc dimethyldithiocarbamate,
zinc ethylenebisdithiocarbamate,
manganese ethylenebisdithiocarbamate,
maganese zinc ethylenediaminebisdithiocarbamate,
tetramethylthiuram disulfide, ammonia complex of zinc (N,N-ethylenebisdithiocarbamate),
ammonia complex of zinc (N,N'-propylenebisdithiocarbamate),
zinc (N,N'-propylenebisdithiocarbamate),
N,N'-polypropylenebis(thiocarbamoyl)disulfide;
nitro derivatives, such as
dinitro(1-methylheptyl)phenyl crotonate,
2-sec-butyl-4,6-dinitrophenyl-3,3-dimethyl acrylate,
2-sec-butyl-4,6-dinitrophenylisopropyl carbonate,
di-isopropyl 5-nitroisophthalate;
heterocyclic substance, such as
2-heptadecyl-2-imidazoline acetae,
2,4-dichloro-6-(o-chloroanilino)-s-triazine,
O,O-diethyl phthalimidophosphonothioate,
5-amino-1-[bis-(dimethylamino)-phosphinyl]-3-phenyl-1,2,4-triazole,
2,3-dicyano-1,4-dithioanthraquinone,
2-thio-1,3-dithiolo[4,5-b]quinoxaline,
methyl 1-(butylcarbamoyl)-2-benzimidazolecarbamate,
2-methoxycarbonylaminobenzimidazole,
2-(furyl-(2))benzimidazole,
2-(thiazolyl-(4))benzimidazole, N-(1,1,2,2-tetrachloroethylthio)tetrahydrophthalimide,
N-trichloromethylthiotetrahydrophthalimide,
N-trichloromethylthiophthalimide,
N-dichlorofluoromethylthio-N',N'-dimethyl-N-phenylsulfuric diamide,
5-ethoxy-3-trichloromethyl-1,2,3-thiadiazole,
2-thiocyanatomethylthiobenzothiazole,
1,4-dichloro-2,5-diemthoxybenzene,
4-(2-chlorophenylhydrazono)-3-methyl-5-isoxazolone,
pyridine 2-thio-1-oxide,
8-hydroxyquinoline or its copper salt,
2,3-dihydro-5-carboxanilido-6-methyl-1,4-oxathiine,
2,3-dihydro-5-carboxanilido-6-methyl-1,4-oxathiine 4,4-dioxide,
2-methyl-5,6-dihydro-4H-pyran-3-carboxanilide,
2-methylfuran-3-carboxanilide,
2,5-dimethylfuran-3-carboxanilide,
2,4,5-trimethylfuran-3-carboxanilide,
N-cyclohexyl-2,5-dimethylfuran-3-carboxamide,
N-cyclohexyl-N-methoxy-2,5-dimethylfuran-3-carboxamide,
2-methylbenzanilide,
2-iodobenzanilide,
N-formyl-N-morpholine-2,2,2-trichloroethyl acetate,
piperazine-1,4-diylbis(1-(2,2,2-trichloroethyl)formamide,
1-(3,4-dichloroanilino)-1-formylamino-2,2,2-trichloroethane,
2,6-dimethyl-N-tridecyl-morpholine or its salts,
2,6-dimethyl-N-cyclododecylmorpholine or its salts,
N-[3-(p-tert-butylphenyl)-2-methylpropyl]-cis-2,6-dimethylmorpholine,
N-[3-(p-tert-butylphenyl)-2-methylpropyl]piperidine,
1-[2-(2,4-dichlorophenyl)-4-ehtyl-1,3-dioxolan-2-yl-ethyl]-1H-1,2,4-triazole,
1-[2-(2,4-dichlorophenyl)-4-n-propyl-1,3-dioxolan-2-yl-ethyl]-1H-1,2,4-triazole,
N-(n-propyl)-N-(2,4,6-trichlorophenoxyethyl)-N'-imidazolylurea,
1-(4-chlorophenoxy)-3,3-dimethyl-1-(1H-1,2,4-triaxol-1-yl)-2-butanone,
1-(4-chlorophenyl)-3,3-dimethyl-1-(1H-1,2,4-triazol-1-yl)-2-butanol,
α-(2-chlorophenyl)-α-(4-chlorophenyl)-5-pyrimidinemethanol,
5-butyl-2-dimethylamino-4-hydroxy-6-methylpyrimidine,
bis(p-chlorophenyl)-3-pyridinemethanol,
1,2-bis(3-ethoxycarbonyl-2-thioureido)benzene,
1,2-bis(3-methoxycarbonyl-2-thioureido)benzene,
and a variety of fungicides, such as
dodecylguanidine acetate,
3-[3-(3,5-dimethyl-2-oxycyclohexyl)-2-hydroxyethyl]-glutarimide,
hexachlorobenzene,
methy N-(2,6-diemthylphenyl)-N-(2-furoyl)-DL-alaninate,
DL-N-(2,6-diemthylphenyl)-N-(2'-methoxyacetyl)-alanine methyl ester,
N-(2,6-diemthylphenyl)-N-chloroacetyl-D,L-2-aminobutyrolactone,
DL-N-(2,6-dimethylphenyl)-N-(phenylacetyl)alanine methyl ester,
5-methyl-5-vinyl-3-(3,5-dichlorophenyl)-2,4-dioxo-1,3-oxazolidine,
3-[3,5-dichlorophenyl-(5-methyl-5-methoxymethyl]-1,3-oxazolidine-2,4-dione,
3-(3,5-dichlorophenyl)-1-isopropylcarbamoylhydantoin,
N-(3,5-dichlorophenyl)-1,2-dimethylcyclopropane-1,2-dicarboximide,
2-cyano-[N-(ethylaminocarbonyl)-2-methoximino]acetamide,
1-[2-(2,4-dichlorophenyl)pentyl]-1H-1,2,4-triazole,
2,4-difuloro-α-(1H-1,2,4-triazolyl-1-methyl)benzhydryl alcohol,
N-(3-chloro-2,6-dinitro-4-trifluoromethylphenyl)-5-trifluoromethyl-3-chloro-2-aminopyridine,
1-((bis(4-fluorophenyl)methylsilyl)methyl-1H-1,2,4-triazole.

The synergistic action of the compositions according to the invention is illustrated with the aid of the following use examples:

USE EXAMPLE 1

Activity against *Botrytis cinerea*

Bell pepper seedlings cv. "Neusiedler Ideal Elite" were sprayed to drip point with aqueous suspensions comprising 80% of active ingredient and 20% of emulsifier in the dry matter after 4–5 leaves had developed properly. After the spray coating had dried on, the plants were sprayed with a conidia suspension of the fungus *Botrytis cinerea* and placed into a chamber at 22–24° C. at high atmospheric humidity. After 5 days, the disease on the untreated control plants had developed to such an extent that the foliar necroses formed covered most of the leaf area (disease level 83%). The amide compounds used were compounds I.1 and I.2, of the formulae

I.1

I.2

The visually determined data for the percentage of diseased leaf area were converted into efficacy levels as a percentage of the untreated control. An efficacy of O indicates the same disease level as in the untreated control, an efficacy of 100 indicates a disease level of 0%. The expected efficacies of active ingredient combinations were determined using Colby's formula (Colby, S. R. (Calculating synergistic and antagonistic responses of herbicide Combinations", Weeds, 15, pp. 20–22, 1967) and compared with the observed efficacies. The results are shown in Table 1 below.

TABLE 1

| Active Ingredient | Concentration of Active Ingredient [ppm] | | Efficacy Level in % of Control | |
|---|---|---|---|---|
| | Fenazaquin | Active Ingredient I.1 or I.2 | observed | calculated*) |
| Control (untreated) | — | — | 0 | |
| (Fenazaquin) | 250 | — | 4 | |
| I.1 | — | 31 | 70 | |
| | — | 16 | 64 | |
| I.2 | — | 31 | 40 | |
| | — | 16 | 4 | |
| Fenazaquin + I.1 | 250 | 31 | 88 | 71 |
| | 250 | 16 | 76 | 65 |
| Fenazaquin + I.2 | 250 | 31 | 63 | 42 |
| | 250 | 16 | 52 | 8 |

*)calculated by using Colby's formula

It can be seen from the experimental results that the observed efficacy in all mixing ratios exceeds the additive efficacy calculated beforehand using Colby's formula, ie. a synergistic effect is present.

USE EXAMPLE 2
Activity against *Botrytis cinerea* on bell pepper fruits

Discs of green bell pepper fruits were sprayed to drip point with an aqueous preparation of the active ingredient comprising 80% of active ingredient and 20% of emulsifier in the dry matter. 2 hours after the spray coating had dried on, the fruit discs were inoculated with a spore suspension of *Botrytis cinerea* containing $1.7 \times 10^6$ spores per ml of a 2% strength Biomalz solution. The inoculated fruit discs were subsequently incubated for 4 days in humid chambers at 18° C. The botrytis development on the infected fruit discs was then assessed visually (disease level 94%). The amide compounds employed were the above compounds II and III.

The visually determined data for the percentage of diseased leaf area were converted into efficacy levels as a percentage of the untreated control. An efficacy of O indicates the same disease level as in the untreated control, an efficacy of 100 indicates a disease level of 0%. The expected efficacies of active ingredient combinations were determined using Colby's formula (Colby, S. R. (Calculating synergistic an dantagonistic responses of herbicide Combinations", Weeds, 15, pp. 20–22, 1967) and compared with the observed efficacies. The results are shown in Table 2 below.

TABLE 2

| Active Ingredient | Concentration of Active Ingredient [ppm] | | Efficacy Level in % of Control | |
|---|---|---|---|---|
| | Fenazaquin | Active Ingredient I.1 or I.2 | observed | calculated*) |
| Control (untreated) | — | — | 0 | |
| Fenazaquin | 250 | — | 15 | |
| I.1 | — | 31 | 68 | |
| I.2 | — | 31 | 95 | |
| | — | 16 | 36 | |
| Fenazaquin + I.1 | 250 | 31 | 89 | 73 |
| Fenazaquin + I.2 | 250 | 31 | 100 | 95 |
| | 250 | 16 | 95 | 45 |

*)calculated by using Colby's formula

It can be seen from the experimental results that the observed efficacy in all mixing ratios exceeds the additive efficacy calculated beforehand using Colby's formula, ie. a synergistic effect is present.

Similar results are obtained when the amide compound used is one of the compounds mentioned in Table 3 below, of the formula Ia:

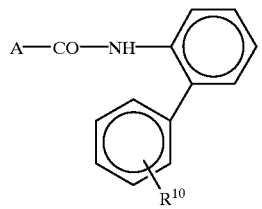

where A is

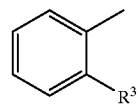

(A1)

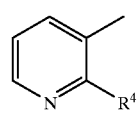

(A2)

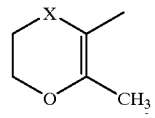

(A3)

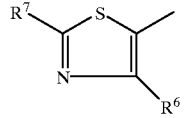

(A5)

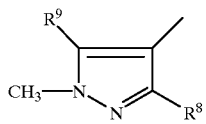

(A7)

or another individual compound mentioned in EP-A-545 099 and 589 301.

TABLE 3

| Nr. | A | R³ | R⁴ | R⁵ | R⁶ | R⁷ | R⁸ | R⁹ | R¹⁰ | X | phys. Data [° C.] |
|---|---|---|---|---|---|---|---|---|---|---|---|
| 3.1 | A₁ | CH₃ | — | — | — | — | — | — | 2-F | — | |
| 3.2 | A₁ | CH₃ | — | — | — | — | — | — | 4-F | — | |
| 3.3 | A₁ | CH₃ | — | — | — | — | — | — | 2-F | — | |
| 3.4 | A₁ | CF₃ | — | — | — | — | — | — | 4-F | — | |
| 3.5 | A₂ | — | Cl | — | — | — | — | — | 2-F | — | |
| 3.6 | A₂ | — | Cl | — | — | — | — | — | 2-CH₃ | — | 71–73 |
| 3.7 | A₂ | — | Cl | — | — | — | — | — | 2-Cl | — | |
| 3.6 | A₂ | — | Cl | — | — | — | — | — | 2-OCH₃ | — | |
| 3.9 | A₂ | — | Cl | — | — | — | — | — | 3-F | — | |
| 3.10 | A₂ | — | Cl | — | — | — | — | — | 3-Cl | — | 95–98 |
| 3.11 | A₂ | — | Cl | — | — | — | — | — | 3-CH₃ | — | |
| 3.12 | A₂ | — | Cl | — | — | — | — | — | 3-OCH₃ | — | |
| 3.13 | A₂ | — | Cl | — | — | — | — | — | 3-OiC₃H₇ | — | |
| 3.14 | A₂ | — | Cl | — | — | — | — | — | 3-Br | — | |
| 3.15 | A₂ | — | Cl | — | — | — | — | — | 4-F | — | 156–157 |
| 3.16 | A₂ | — | Cl | — | — | — | — | — | 4-Cl | — | 142–144 |
| 3.17 | A₂ | — | Cl | — | — | — | — | — | 4-CH₃ | — | 115–117 |
| 3.18 | A₂ | — | Cl | — | — | — | — | — | 4-OCH₃ | — | 114–116 |
| 3.19 | A₂ | — | Cl | — | — | — | — | — | 4-SCH₃ | — | |
| 3.20 | A₃ | — | — | — | — | — | — | — | 2-F | CH₂ | |
| 3.21 | A₃ | — | — | — | — | — | — | — | 3-F | CH₂ | |
| 3.22 | A₃ | — | — | — | — | — | — | — | 4-F | CH₂ | |
| 3.23 | A₃ | — | — | — | — | — | — | — | 3-Cl | CH₂ | |
| 3.24 | A₃ | — | — | — | — | — | — | — | 3-CH₃ | CH₂ | |
| 3.25 | A₃ | — | — | — | — | — | — | — | 2-F | S | |
| 3.26 | A₃ | — | — | — | — | — | — | — | 3-F | S | |
| 3.27 | A₃ | — | — | — | — | — | — | — | 4-F | S | |
| 3.28 | A₃ | — | — | — | — | — | — | — | 3-Cl | S | |
| 3.29 | A₃ | — | — | — | — | — | — | — | 3-CH₃ | S | |
| 3.30 | A₃ | — | — | — | — | — | — | — | 2-F | SO₂ | |
| 3.31 | A₃ | — | — | — | — | — | — | — | 3-F | SO₂ | |
| 3.32 | A₃ | — | — | — | — | — | — | — | 4-F | SO₂ | |
| 3.33 | A₃ | — | — | — | — | — | — | — | 3-Cl | SO₂ | |
| 3.34 | A₃ | — | — | — | — | — | — | — | 3-CH₃ | SO₂ | |
| 3.35 | A₅ | — | — | — | CF₃ | CH₃ | — | — | 2-F | — | |
| 3.36 | A₅ | — | — | — | CF₃ | CH₃ | — | — | 3-F | — | |
| 3.37 | A₅ | — | — | — | CF₃ | CH₃ | — | — | 4-F | — | |
| 3.38 | A₇ | — | — | — | — | — | CH₃ | Cl | 2-F | — | |
| 3.39 | A₇ | — | — | — | — | — | CH₃ | Cl | 3-F | — | |
| 3.40 | A₇ | — | — | — | — | — | CH₃ | Cl | 4-F | — | |
| 3.41 | A₇ | — | — | — | — | — | CF₃ | Cl | 2-F | — | |
| 3.42 | A₇ | — | — | — | — | — | CF₃ | Cl | 4-F | — | |

We claim:

1. A composition for controlling harmful fungi, which comprises a solid or liquid carrier and synergistically effective amounts of a) fenazaquin, of the formula I

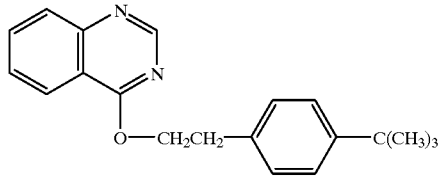

and b) at least one amide compound of the formula II $$A-CO-NR^1R^2 \quad (II)$$

wherein

A is pyridyl which is unsubstituted or substituted by 1, 2 or 3 substituents selected from the group consisting of alkyl, halogen, $CHF_2$ and $CF_3$;

$R^1$ is a hydrogen atom;

$R^2$ is a phenyl or cycloalkyl group which is unsubstituted or substituted by 1, 2 or 3 substituents selected from the group consisting of alkyl, alkenyl, alkynyl, alkynyl, alkoxy, alkenyloxy, alkynyloxy, cycloalkyl, cycloalkenyl, cycloalkoxy, cycloalkenyloxy, phenyl and halogen, it being possible for the aliphatic and cycloaliphatic radicals to be partially or fully halogenated and/or for the cycloaliphatic radicals to be substituted by 1 to 3 alkyl groups, and it being possible for the phenyl group to be substituted by 1 to 5 halogen atoms and/or 1 to 3 substituents selected from the group consisting of alkyl, haloalkyl, alkoxy, haloalkoxy, alkylthio and haloalkylthio, and it being possible for the amidic phenyl group to be fused to a saturated 5-membered ring which is unsubstituted or substituted by one or more alkyl groups and/or can have, as a ring member, a hetero atom selected from the group consisting of O and S.

2. The composition defined in claim 1, wherein A is pyridin-3-yl which is unsubstituted or substituted in the 2-position by halogen, methyl, difluoromethy or trifluoromethyl.

3. The composition defined in claim 1, wherein the amide compound is of the formula IIa (IIa)

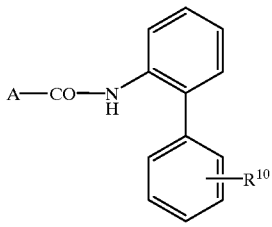

wherein

A is a pyridyl group of formula A2

(A2)

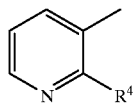

wherein

R⁴ is trifluoromethyl or chlorine

R¹⁰ is $C_1$–$C_4$-alkyl, $C_1$–$C_4$-alkoxy, $C_1$–$C_4$-alkylthio or halogen.

4. The composition defined in claim 1, wherein the amide compound is of the formula IIb (IIb)

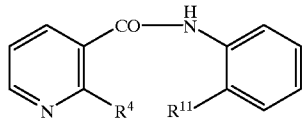

where

R⁴ is halogen and

R¹¹ is phenyl which is substituted by halogen.

5. The composition defined in claim 1, wherein the amide compound is of one of the following formulae:

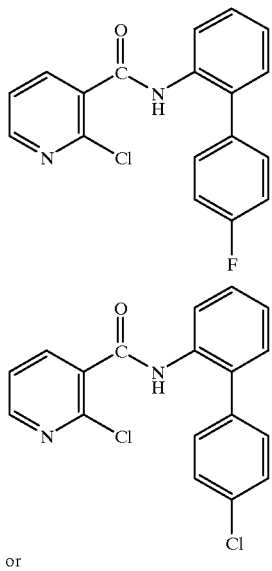

or

-continued

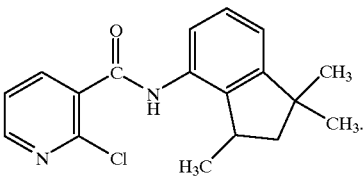

6. The composition defined in claim 1, which is formulated in two parts, one part comprising fenazaquin in a solid or liquid carrier and the other part comprising the amide compound in a solid or liquid carrier.

7. The composition defined in claim 1, wherein

A is pyrindin-3-yl which is unsubstituted or substituted by 1,2 or 3 substituents selected from the group consisting of alkyl, halogen, $CHF_2$ and $CF_3$, and R² is phenyl which is unsubstituted or substituted by 1, 2 or 3 substituents selected from the group consisting of alkyl, alkenyl, alkynyl, alkoxy, alkenyloxy, alkynyloxy, cycloalkyl, cycloalkenyl, cycloalkoxy, cycloalkenyloxy, phenyl and halogen, it being possible for the aliphatic and cycloaliphatic radicals to be partially or fully halogenated, and for the cycloaliphatic radicals to be substituted by 1 to 3 alkyl groups, and it being possible for the phenyl group to be substituted by 1 to 5 halogen atoms and/or 1 to 3 substituents selected from the group consisting of alkyl, haloalkyl, alkoxy, haloalkoxy, alkylthio and haloalkythio, and it being possible for the amidic phenyl group to be fused to a saturated 5-membered ring which is unsubstituted or substituted by one or more alkyl groups and/or can have, as a ring member, a hetero atom selected from the group consisting of O and S.

8. The composition defined in claim 1, wherein

A is pyridyl which is unsubstituted or substituted by 1, 2 or 3 substituents selected from the group consisting of alkyl, halogen, difuloromehtyl and trifluoromethyl, and R² is phenyl which is substituted by one of the following substituents in the 2-position: $C_3$–$C_6$-alkyl, $C_5$–$C_6$-cycloalkenyl, $C_5$–$C_6$-cycloalkoxy, cycloalkenyloxy, which groups are unsubstituted or substituted by 1, 2 or 3 $C_1$–$C_4$-alkyl groups.

9. The composition defined in claim 1, wherein A is a radical of the formula (A2)

(A2)

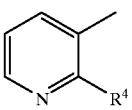

wherein R⁴ is trifluoromethyl or chlorine.

10. A method of controlling harmful fungi, which comprises treating the fungi, their environment, or materials, plants, seeds, soils, areas or spaces to be protected against fungal infection, with a fungicidally effective amount of a composition defined in claim 1, it being possible to apply the active ingredients fenazaquin and the amide compound simultaneously or in succession.

11. The method of claim 10, wherein

A is pyridin-3-yl which is unsubstituted or substituted by 1, 2 or 3 substituents selected from the group consisting of alkyl, halogen, $CHF_2$ and $CF_3$, and R² is phenyl which is unsubstituted or substituted by 1, 2 or 3 substituents selected from the group consisting of alkyl, alkenyl, alkynyl, alkoxy, alkenyloxy, alkynyloxy, cycloalkyl, cycloalkenyl, cycloalkoxy, cycloalkenyloxy, phenyl and halogen, it being possible for the aliphatic and cycloaliphatic radicals to be partially or fully halogenated, and for the cycloaliphatic radicals to be substituted by 1 to 3 alkyl groups, and it being possible for the phenyl group to be substituted by 1 to 5 halogen atoms and/or 1 to 3 substituents selected from the group consisting of alkyl, haloalkyl, alkoxy, haloalkoxy, alkylthio and haloalkylthio, and it being possible for the amidic phenyl group to be fused to a saturated 5-membered ring which is unsubstituted or substituted by one or more alkyl groups and/or can have, as a ring member, a hetero atom selected from the group consisting of O and S.

12. The method of claim 10, wherein
A is pyridyl which is unsubstituted or substituted by 1, 2 or 3 substituents selected from the group consisting of alkyl, halogen, difluoromethyl and trifluoromethyl, and
$R^2$ is phenyl which is substituted by one of the following substituents in the 2-position: $C_3$–$C_6$-alkyl, $C_5$–$C_6$-cycloalkenyl, $C_5$–$C_6$-cycloalkoxy, cycloalkenyloxy, which groups are unsubstituted or substituted by 1, 2 or 3 $C_1$–$C_4$-alkyl groups.

13. The method of claim 1, wherein A is of the formula (A2)

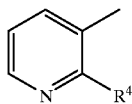

(A2)

wherein $R^4$ is trifluoromethyl or chlorine.

14. The method of claim 1, wherein $R^2$ is a radical of the formula

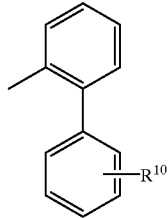

wherein $R^{10}$ is $C_1$–$C_4$-alkyl, $C_1$–$C_4$-alkoxy, $C_1$–$C_4$-alkylthio or halogen.

15. The method of claim 1, wherein the amide compound is of the formula IIb

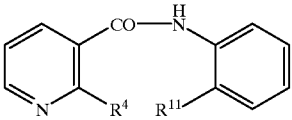

(IIb)

where $R^4$ is halogen and $R^{11}$ is phenyl which is substituted by halogen.

16. The method of claim 10, wherein the amide compound is of one of the following formulae:

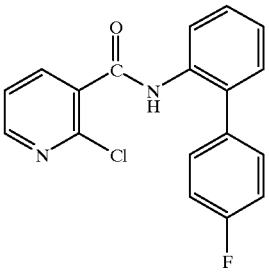

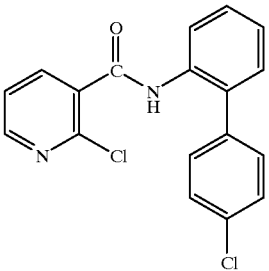

or

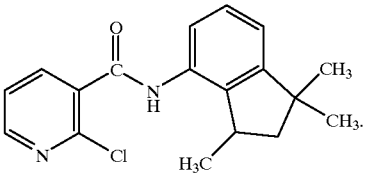

* * * * *

UNITED STATES PATENT AND TRADEMARK OFFICE
CERTIFICATE OF CORRECTION

PATENT NO.: 6,130,224

DATED: October 10, 2000

INVENTOR(S): EICKEN et al.

It is certified that error appears in the above-identified patent and that said Letters Patent is hereby corrected as shown below:

In the abstract, line 1, "composiitons" should be --compositions--.
Col. 1, lines 8 and 27, "analide" should be --anilide--.
Col. 1, line 66, "-X-CH$_2$)m-;" should be -- -X-(CH$_2$)$_m$-;--.
Col. 2, line 56, "alkyloxy" should be --alkynyloxy--.
Col. 3, line 67, "4-alkynyl" should be --4-hexynyl--.
Col. 4, line 9 "applied" should be --applies--.
Col. 8, line 12, "carries" should be --carriers--.
Col. 8, lines 24 and 40, "water" should be --waste--.
Col. 8, line 39, "polyosypropylene" should be --polyoxypropylene--.
Col. 9, line 6, "40 ml" should be --40 mol--.
Col. 10, line 55, "substance" should be --substances--.
Col. 10, line 56, "acetae" should be --acetate--.
Col. 11, line 9, "2,5-diemthoxybenzene" should be --2,5-dimethoxybenzene--.
Col. 11, line 39, "4-ehtyl" should be --4-ethyl--.
Col. 11, line 46, "1,2,4-triaxol" should be --1,2,4-triazol--.
Col. 11, line 64, "methy" should be --methyl--; "2,6-diemthylphenyl" should be
  --2,6-dimethylphenyl--.
Col. 12, line 1, "2,6-diemthylphenyl" should be --2,6-dimethylphenyl--.
Col. 12, line 16, "2,4-difuloro" should be --2,4-difluoro--.
Col. 13, lines 1 and 49, "efficacy of O" should be --efficacy of 0--.
Col. 13, line 54, "an dantagonistic" should be --and antagonistic--.
Col. 13, table 3, Nr: 3.3, "CH$_3$" should be --CF$_3$--.
Col. 15, table 3, Nr. 3.6 on line 8 of the table should be --3.8--.
Col. 16, claim 1, line 44, delete "alkynyl.".
Col. 16, claim 2, line 64, "difluoromethy " should be --difluoromethyl--.

UNITED STATES PATENT AND TRADEMARK OFFICE
CERTIFICATE OF CORRECTION

PATENT NO.: 6,130,224

DATED: October 10, 2000

INVENTOR(S): EICKEN et al.

It is certified that error appears in the above-identified patent and that said Letters Patent is hereby corrected as shown below:

On the cover page, item [22], "Sep. 5, 1996" should be --Sep. 3, 1996--.

Col. 18, claim 8, line 37, "difuloromehtyl" should be --difluoromethyl--.

Col. 18, claim 10, line 57, after "composition" insert --as--.

Col. 19, claim 13, line 21, "claim 1" should be --claim 10--.

Col. 19, claim 14, line 32, "claim 1" should be --claim 10--.

Col. 19, claim 15, line 47, "claim 1" should be --claim 10--.

Signed and Sealed this

Twenty-ninth Day of May, 2001

*Attest:*

NICHOLAS P. GODICI

*Attesting Officer*  *Acting Director of the United States Patent and Trademark Office*